United States Patent
Roth et al.

(10) Patent No.: US 12,420,470 B2
(45) Date of Patent: Sep. 23, 2025

(54) APPARATUS AND METHOD FOR SHAPING PLASTIC PREFORMS INTO PLASTIC CONTAINERS, HAVING A CLEAN ROOM WITH A REMOVABLE COVER APPARATUS

(71) Applicant: KRONES AG, Neutraubling (DE)

(72) Inventors: Andreas Roth, Erlangen (DE); Florian Geltinger, Donaustauf (DE); Christian Wittmann, Hemau (DE); Mathias Burgmeier, Schierling (DE); Christian Huettner, Pfakofen (DE)

(73) Assignee: KRONES AG, Neutraubling (DE)

( * ) Notice: Subject to any disclaimer, the term of this patent is extended or adjusted under 35 U.S.C. 154(b) by 41 days.

(21) Appl. No.: 18/240,909

(22) Filed: Aug. 31, 2023

(65) Prior Publication Data
US 2024/0066784 A1    Feb. 29, 2024

(30) Foreign Application Priority Data
Aug. 31, 2022   (DE) .................... 10 2022 122 085.0

(51) Int. Cl.
*B29C 49/46* (2006.01)
*B29C 49/12* (2006.01)
(Continued)

(52) U.S. Cl.
CPC ............. *B29C 49/46* (2013.01); *B29C 49/12* (2013.01); *B29C 49/42065* (2022.05); *B29C 2049/4697* (2013.01); *B29L 2031/712* (2013.01)

(58) Field of Classification Search
CPC ......... B29C 49/46; B29C 49/42; B29C 49/28; B29C 49/12; B29C 49/42095; B29C 49/42065; B29L 2031/712
See application file for complete search history.

(56) References Cited

U.S. PATENT DOCUMENTS

| 6,134,866 A | 10/2000 | Schoenewolff et al. ........ 53/561 |
| 7,393,373 B1 * | 7/2008 | Krippner ............. B29C 45/1701 55/385.2 |

(Continued)

FOREIGN PATENT DOCUMENTS

| CN | 104339627 | * | 2/2015 | ............. B29C 49/42 |
| CN | 220883358 | | 5/2024 | ............. B29C 49/12 |

(Continued)

OTHER PUBLICATIONS

CN104339627 English translation prepared Dec. 2, 2024 (Year: 2024).*

(Continued)

*Primary Examiner* — Alison L Hindenlang
*Assistant Examiner* — Shibin Liang
(74) *Attorney, Agent, or Firm* — HAYES SOLOWAY P.C.

(57) ABSTRACT

Disclosed is an apparatus for shaping plastic preforms into containers, having a transport device, which transports the plastic preforms to be shaped along a transport path, wherein the transport device has a rotatable transport carrier wherein a plurality of shaping stations are arranged. The shaping stations each have blow-molding devices which the preforms are shaped by applying a flowable medium. The shaping stations have application devices which apply the flowable medium to the preforms, wherein the shaping stations have stretching devices for stretching the preforms in a longitudinal direction. The stretching devices have at least one stretching rod which can be moved in the longitudinal direction of the preforms and can be inserted into the plastic preforms. The device has a clean room, which the plastic preforms are expanded into the plastic containers, and a sealing device to seal the clean room from a non-sterile environment, and closed with a cover device.

12 Claims, 2 Drawing Sheets

(51) Int. Cl.
  B29C 49/42 (2006.01)
  B29L 31/00 (2006.01)

(56) References Cited

U.S. PATENT DOCUMENTS

| | | | | |
|---|---|---|---|---|
| 8,647,101 | B2 | 2/2014 | Quetel et al. | B29C 49/42 |
| 8,770,957 | B2 | 7/2014 | Laumer | B29C 49/36 |
| 8,771,584 | B2 | 7/2014 | Voth | B29C 49/68 |
| 11,072,106 | B2 | 7/2021 | Martini et al. | B29C 49/38 |
| 11,084,202 | B2 | 8/2021 | Hayakawa | B29C 49/36 |
| 2013/0040009 | A1 | 2/2013 | Laumer | B29C 49/30 |
| 2014/0325941 | A1 | 11/2014 | Knott et al. | B65B 55/027 |
| 2018/0009646 | A1 | 1/2018 | Hayakawa et al. | B67C 7/09 |
| 2018/0354670 | A1 | 12/2018 | Schinelli | B65C 9/40 |
| 2020/0198215 | A1 | 6/2020 | Mueller et al. | B29C 49/46 |
| 2023/0001623 | A1 | 1/2023 | Gerhards | B29C 49/42 |
| 2024/0009913 | A1 | 1/2024 | Wittmann et al. | B29C 49/46 |

FOREIGN PATENT DOCUMENTS

| | | |
|---|---|---|
| DE | 102009007138 | 8/2010 |
| DE | 102010032964 | 2/2012 |
| DE | 102013022281 | 2/2015 |
| DE | 102010018582 | 1/2018 |
| DE | 2731631 | 5/2018 |
| DE | 102019128019 | 4/2021 |
| DE | 102019008631 | 6/2021 |
| EP | 2556943 | 6/2018 |
| WO | WO2010020529 | 2/2010 |
| WO | WO2021239936 | 12/2021 |

OTHER PUBLICATIONS

Search Report issued in German Patent Appln. Serial No. 10 2022 122 085.0, dated Mar. 27, 2023, with machine English translation, 9 pages.
Search Report issued in German Patent Appln. Serial No. 10 2022 123 064.3, dated May 15, 2023, with machine English translation, 14 pages.
Search Report issued in European Patent Appln. Serial No. 23 191993.7, dated Dec. 1, 2023, with machine English translation, 19 pages.
Search Report issued in European Patent Appln. Serial No. 23195972.7, dated Feb. 2, 2024, with machine English translation, 15 pages.
Office Action issued in Chinese Application No. 202322327559.2, with machine translation, dated May 8, 2024, 4 pgs.

* cited by examiner

APPARATUS AND METHOD FOR SHAPING PLASTIC PREFORMS INTO PLASTIC CONTAINERS, HAVING A CLEAN ROOM WITH A REMOVABLE COVER APPARATUS

BACKGROUND OF THE INVENTION

The present invention relates to an apparatus and a method for shaping plastic preforms into plastic containers. Such apparatuses and methods have long been known from the prior art. Usually, in this case, heated plastic preforms are shaped into plastic containers by applying a flowable medium—in particular, compressed air.

More recently, sterile apparatuses of this type have also become known to some extent. These have the advantage that plastic preforms can either already come directly from a furnace and are therefore sterile, or have been sterilized by a sterilization apparatus. Subsequently, they can be shaped into the plastic containers in a likewise sterile manner. In this case, such apparatuses typically have clean rooms within which the expansion process takes place.

It has been shown in the prior art that such apparatuses and methods are associated with various technical difficulties—in particular with regard to the size of the respective clean room and keeping the clean room sterile or sterilizing it. In this case—in particular, due to the limited size of the respective clean room—installation, assembly, replacement, or the like of individual modules of the apparatus has proven to be relatively complicated and laborious.

A prime example here is the assembly of transport devices which supply the plastic preforms to the apparatus or via which the plastic containers are discharged from the apparatus, and which are arranged at least in part in the clean room. Due to their own size in conjunction with the limited size of the clean room, these transport devices can be assembled only in the clean room, i.e., a pre-assembly of the transport devices is not possible, which means an exceptionally high expenditure of time for a fitter or operator of the apparatus, and moreover leads to increased cycle times on the conveyer belt.

The present invention is therefore based on the object of providing an assembly and operation-friendly apparatus and method for shaping plastic preforms into plastic containers, having a clean room, in the case of which time expenditure can be saved by installing or removing or exchanging pre-assembled modules.

SUMMARY OF THE INVENTION

An apparatus according to the invention for shaping plastic preforms into plastic containers has a transport device, which transports the plastic preforms to be shaped along a predefined transport path. In this case, the transport device has a rotatable transport carrier on which a plurality of shaping stations are arranged, wherein said shaping stations each have blow-molding apparatuses, within which the plastic preforms can be shaped, and in particular expanded, into the plastic containers, by applying a flowable and in particular gaseous medium. Preferably, the transport path runs circularly.

The shaping stations also each have application devices for applying the flowable medium to the plastic preforms. Furthermore, the shaping stations each have stretching devices for stretching the plastic preforms in their longitudinal direction. These stretching devices each have at least one stretching rod which is movable in the longitudinal direction of the plastic preforms and which can be inserted into the plastic preforms.

Furthermore, the apparatus has a clean room, within which the plastic preforms are expanded or can be expanded into the plastic containers, and a sealing device in order to seal the clean room from a non-sterile environment. Furthermore, this sealing device has at least one and preferably at least two circumferential channels which can be filled or are filled with a liquid.

According to the invention, the clean room is closed with a cover device. In this case, said cover device is designed in such a way that it is removable for assembly purposes. A removal of the cover device in the sense of the present invention can be a partial or complete removal of the cover device from the clean room. Complete removal of the cover device from the clean room is to be understood to mean that the cover device is removed completely in its entirety. Partial removal of the cover device from the clean room is to be understood to mean that the cover device can be pivoted away or folded away from the clean room by means of corresponding hinges or the like, for example.

In a first preferred embodiment, the cover device is detachably connected to the clean room, or the cover device can be detached from the clean room. In particular, the clean room can be opened in this way.

In a further preferred embodiment, the cover device delimits the clean room at the top. Particularly preferably, the cover device is formed in a roof of the clean room.

In a further preferred embodiment, the cover device is designed as a non-supporting device.

An embodiment as a non-supporting device is understood to mean, in particular, that the cover device of the clean room is neither suitable nor intended for carrying components of the apparatus, such as drives, shaping stations, and the like.

The cover device can thus be manufactured, for example, in a material thickness and/or a material that does not enable a supporting and/or bracing function.

In a further preferred embodiment, the cover device is mounted in a floating manner. In particular, it can therefore move within predetermined limits in a horizontal direction. This is non-critical, since, as mentioned above, the cover device is preferably not designed as a supporting device.

In a further preferred embodiment, the cover device has a substantially circular or annular shape. Likewise, in a further preferred embodiment, the clean room has a substantially circular or annular recess. In this case, a preferred embodiment provides that the substantially circular or annular shape of the cover device is larger than the substantially circular or annular recess of the clean room.

The most important reason for a circular or annular shape of the cover device and of the clean room is that the cover device cannot fall into the clean room lying underneath during assembly work when the cover device is positioned obliquely. This is due to the circular shape of the cover. All sides are of equal length, measured from the center point. If, in contrast, an angular cover device is positioned diagonally on the clean room, this can easily fall in.

In a further preferred embodiment, a projection is formed in the region of the recess of the clean room, which projection is suitable and intended for the cover device to rest upon. Due to the circular or annular shape of the cover device, this rests substantially better in the projection of the clean room than in the case of an angular embodiment of the cover device, since these also do not clatter.

Particularly preferably, a circumferential projection is formed in the region of the recess of the clean room, in a manner similar to a frame. Alternatively, the projection can also be in the form of a pin, a cone, or the like in the region of the recess of the clean room. In addition, however, any other receiving or supporting elements can also be formed in the region of the recess of the clean room which are suitable and intended for the cover device to rest upon.

In a further preferred embodiment, the plastic preforms can be supplied via a second transport device of the apparatus, and can be transported away via a third transport device of the apparatus. Advantageously, the second transport device is therefore a supply device, and the third transport device is a discharge device.

The second transport device is preferably arranged at least in sections within the clean room. Likewise, the third transport device is preferably arranged at least in sections within the clean room. Advantageously, the second transport device is designed as a supporting device. The third transport device is also advantageously designed as a supporting device. Particularly preferably, both the second and the third transport devices, and in particular both the supply and the discharge devices, are designed as supporting devices.

In a further preferred embodiment, the first and/or second transport devices can be inserted or removed via the recess of the clean room.

In this case, a particularly preferred embodiment provides that the first and/or second transport devices be designed as transport starwheels.

The transport starwheel of the second transport device is preferably a pitch division starwheel.

In this case, a further particularly preferred embodiment provides that the transport starwheels be able to be inserted or removed via the recess of the clean room as pre-assembled transport starwheels.

By means of the above-described apparatus, any pre-assembled modules, and preferably transport starwheels, can be inserted or removed in a very simple and uncomplicated manner via the recess of the clean room. This installation or removal or the replacement of pre-assembled modules, and particularly preferably pre-assembled transport starwheels, can also save time, since the transport starwheels can be mounted on the conveyer belt in a very simple manner, instead of the laborious and complicated assembly of the transport starwheels in the clean room that is known previously from the prior art.

The present invention is furthermore directed at a method for shaping plastic preforms into plastic containers, wherein a transport device transports the plastic preforms to be shaped along a predetermined transport path, and wherein the transport device has a rotatable transport carrier on which a plurality of shaping stations are arranged, wherein these shaping stations each have blow-molding devices within which the plastic preforms are shaped into the plastic containers by application of a flowable medium, and the shaping stations each have application devices which apply the flowable medium, and in particular gaseous medium (and in particular sterile air), to the plastic preforms, wherein the shaping stations each have stretching devices for stretching the plastic preforms in the longitudinal direction thereof, or stretching devices which stretch the plastic preforms in the longitudinal direction thereof, and these stretching devices each have at least one stretching rod which can be moved and/or moves in the longitudinal direction of the plastic preforms and which is introduced into the plastic preforms.

Furthermore, the apparatus has a clean room, within which the plastic preforms are expanded into plastic containers, and a sealing device, which seals the clean room from a non-sterile environment. In this case, the sealing device preferably has at least one circumferential channel filled with a liquid.

According to the invention, the clean room is closed with a cover device. In this case, said cover device is designed such that it is removable for assembly purposes.

In this case, the above-described apparatus is in particular designed and provided to carry out this described method, i.e., all listed features of the above-described apparatus are also disclosed for the method described here, and vice versa.

Further advantages and embodiments emerge from the accompanying drawings,

DETAILED DESCRIPTION OF THE INVENTION

Figure 1:
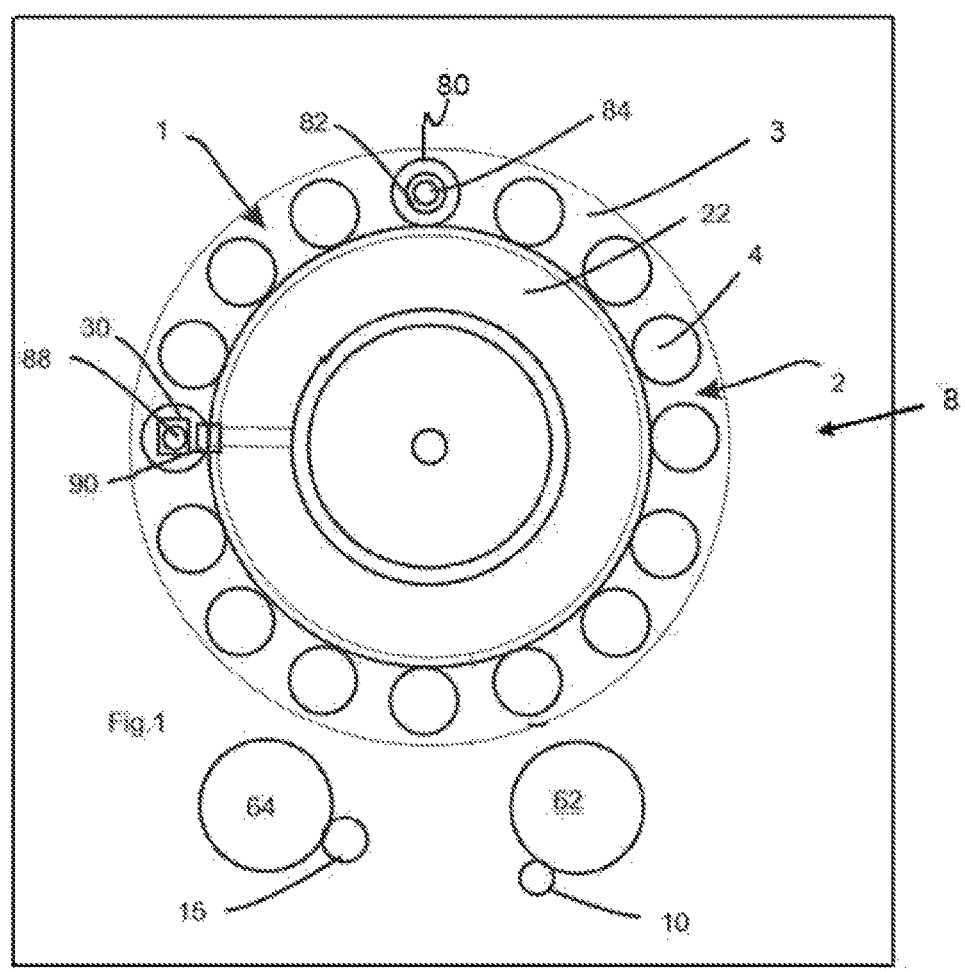
FIG. 1 shows a schematic view of an apparatus according to the invention.

FIG. 1 shows an apparatus 1 for shaping plastic preforms 10 into plastic containers 15. This apparatus has a shaping device 3 having a first transport device 2 having a rotatable transport carrier 22 on which a plurality of shaping stations 4 are arranged. These individual shaping stations 4 each have blow-molding devices 82, which, in their interiors, form a cavity for expanding the plastic preforms 10.

Reference sign 84 denotes an application device, which is used to expand the plastic preforms 10. This can be a blow nozzle, for example, which can be applied to a mouth of the plastic preforms 10 in order to expand them. In addition, it would also be conceivable for the blow-molding nozzle to provide a seal on the blow mold and/or a supporting ring of the plastic preform 10 and/or in the interior of the mouth of the plastic preform 10 and/or at the mouth edge of the plastic preform 10.

Reference sign 90 denotes a valve arrangement, such as a valve block, which preferably has a plurality of valves that control the application of different pressure levels to the plastic preforms 10.

Reference sign 88 denotes a stretching rod used to stretch the plastic preforms in their longitudinal direction. Preferably, all shaping stations 4 have such blow molds 82, application devices 84, and stretching rods 88. This stretching rod is preferably a component of a stretching device denoted by 30.

Preferably, the number of said shaping stations 4 is between 2 and 100, preferably between 4 and 60, and preferably between 6 and 40.

The plastic preforms 10 are supplied via a second transport devices 62 of the apparatus 1. The plastic containers 15 are transported away via a third transport device 64. Thus, the second transport device 62 is preferably a supply device, and the third transport device 64 is a discharge device. In this case, the first and/or second transport devices 62, 64 are preferably designed as transport starwheels.

The reference sign 8 designates a clean room, which is preferably designed such that it surrounds at least the transport path of the plastic preforms 10. In this schematic view, the clean room 8 is shown merely schematically as a rectangle. Preferably, the clean room 8 is sealed from the non-sterile environment by a sealing device, which preferably has at least one water lock.

Preferably, elements of the second transport device 62 and the third transport device 64 are also arranged within the clean room 8. In particular, the clean room 8 preferably also surrounds the transport path of the plastic 30 preforms 10 or plastic containers 15 in the region of the second and third transport devices 62, 64.

Furthermore, the apparatus 1 has a cover device 25 (not shown in FIG. 1), which delimits the clean room 8 at the top.

Figure 2:
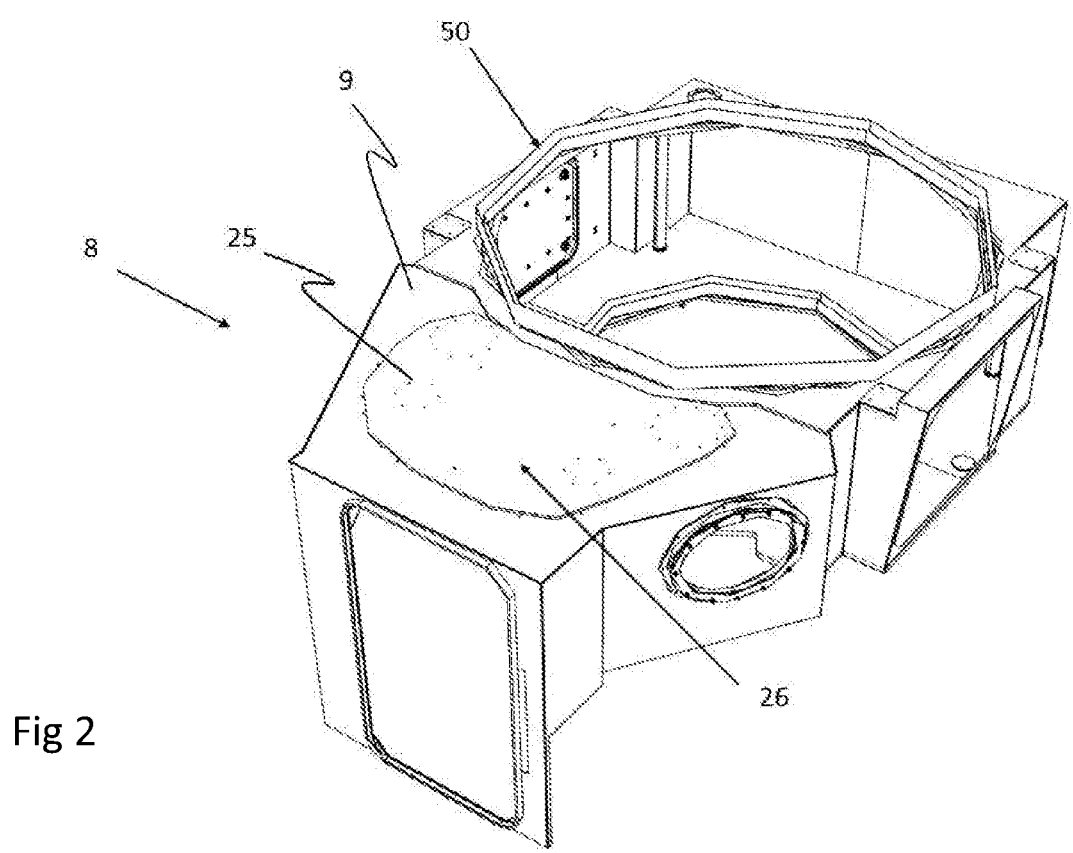
FIG. 2 shows a partial view of the clean room 8 of the apparatus according to the invention.

FIG. 2 is a view of the clean room 8 of the device 1 according to the invention (see FIG. 1 in this regard), which can be closed with a cover apparatus 25 formed to correspond to the recess 26.

As shown here, the cover device 25 is preferably formed in a roof 9 of the clean room 8 and delimits the clean room 8 at the top. The clean room 8 and the cover device 25 have a substantially circular or annular shape or recess 26. In this case, the substantially circular or annular shape of the cover device 25 is larger than the substantially circular or annular recess 26 of the clean room 8.

In this case, the cover device 25 (as is not shown in FIG. 2) can be completely removed, i.e., the cover device 25 is taken off from the clean room 8.

According to the invention, the cover device 25 is designed such that it is removable for assembly purposes, i.e., the cover device 25 is preferably detachably connected to the clean room 8, or the cover device 25 is detachable from the clean room 8. In this way, the clean room 8 can be opened.

As shown here, a projection is formed in the region of the recess 26 of the clean room 8, which projection is suitable and intended for the cover device to rest upon. Here, the projection is designed as a circumferential projection in the region of the recess 26 of the clean room 8. Other embodiments can also have other projections or receiving or support elements in the region of the recess 26 of the clean room 8, as long as they allow the cover device 25 to rest thereon.

Thus, the first and/or second transport devices 62, 64 shown in FIG. 1, which are preferably designed as preassembled transport starwheels, can be inserted or removed very easily and in an uncomplicated manner via the recess 26 of the clean room 8. In general, any pre-assembled modules can be inserted into the clean room 8 or removed via this recess 26 of the clean room 8. This achieves an enormous savings in time compared to the previous assembly of the modules in the clean room 8.

The applicant reserves the right to claim all features disclosed in the application documents as essential to the invention, provided that they are novel over the prior art individually or in combination. It is also pointed out that features which can be advantageous in themselves are also described in the individual figures. A person skilled in the art will immediately recognize that a particular feature described in a figure can be advantageous even without the adoption of further features from this figure. Furthermore, a person skilled in the art will recognize that advantages can also result from a combination of several features shown in individual or in different figures.

LIST OF REFERENCE SIGNS 1 apparatus
2 first transport device
3 shaping device
4 shaping station
8 clean room
9 roof
10 plastic preform
15 plastic container
22 transport carrier
25 cover device
26 recess
30 stretching device
50 sealing device
62 second transport device, transport starwheel
64 third transport device, transport starwheel
80 blow mold
82 blow-molding device
84 application device
88 stretching rod
90 valve assembly
L longitudinal direction

The invention claimed is:

1. An apparatus for shaping plastic preforms into plastic containers, having a first transport device, which transports the plastic preforms to be shaped along a predetermined transport path, wherein the transport device has a rotatable transport carrier on which a plurality of shaping stations are arranged, wherein these shaping stations each have blow-molding devices within which the plastic preforms can be shaped into the plastic containers by applying a flowable medium thereto, and the shaping stations each have application devices in order to apply the flowable medium to the plastic preforms, wherein the shaping stations each have stretching devices for stretching the plastic preforms in the longitudinal direction thereof, and these stretching devices each have at least one stretching rod which can be moved in the longitudinal direction of the plastic preforms and which can be inserted into the plastic preforms, and wherein the apparatus has a clean room, within which the plastic preforms are expanded into the plastic containers, and a sealing device in order to seal the entire clean room from a non-sterile environment, wherein
the entire clean room is closed with a removable cover device, and this removable cover device is designed such that it can be removed for assembly purposes, and wherein a second and/or third transport device is designed as transport starwheels and the transport starwheels are insertable or removable as preassembled transport starwheels via the recess of the clean room.

2. The apparatus according to claim 1,
wherein
the removable cover device is detachably connected to the clean room.

3. The apparatus according to claim 1,
wherein the removable cover device delimits the clean room at the top and is formed in the roof of the clean room.

4. The apparatus according to claim 1,
wherein
the removable cover device is designed as a non-supporting device.

5. The apparatus according to claim 1,
wherein
the removable cover device is mounted in a floating manner.

6. The apparatus according to claim 1,
wherein
the removable cover device has a substantially circular or annular shape.

7. The apparatus according to claim 1, wherein
the clean room has a substantially circular or annular recess.

8. The apparatus according to claim 1, wherein
the substantially circular or annular shape of the removable cover device is larger than the substantially circular or annular recess of the clean room.

9. The apparatus according to claim 1, wherein
a projection is formed in the region of the recess of the clean room, which projection is configured for the removable cover device to rest upon.

10. The apparatus according to claim 1, wherein
the plastic preforms can be supplied via the second transport device of the apparatus, and the plastic containers can be transported away via the third transport device of the apparatus.

11. The apparatus according to claim 1, wherein
the second and/or third transport devices can be inserted or removed via the recess of the clean room.

12. A method for shaping plastic preforms into plastic containers, wherein a first transport device transports the plastic preforms to be shaped along a predetermined transport path, wherein the transport device has a rotatable transport carrier on which a plurality of shaping stations are arranged, wherein these shaping stations each have blow-molding devices within which the plastic preforms can be shaped into the plastic containers by applying a flowable medium thereto, and the shaping stations each have application devices which apply the flowable medium to the plastic preforms, wherein the shaping stations each have stretching devices for stretching the plastic preforms in the longitudinal direction thereof, and these stretching devices each have at least one stretching rod which can be moved in the longitudinal direction of the plastic preforms and which can be inserted into the plastic preforms, and wherein an apparatus has a clean room, within which the plastic preforms are expanded into the plastic containers, and a sealing device which seals the entire clean room from a non-sterile environment,
wherein
the entire clean room is closed with a removable cover device, and this removable cover device is designed such that it can be removed for assembly purposes.

* * * * *